United States Patent
Bresler et al.

[11] Patent Number: 6,102,915
[45] Date of Patent: Aug. 15, 2000

[54] HIP PROSTHESIS POSITIONING INSTRUMENT

[75] Inventors: Franck Bresler, Nancy; Philippe Catier, Pace; Philippe Caudal, La Croix-Valmer; Jean-Marie Francois, Marienthal; Jean Godefroy, Ayze, all of France; Henri Horoszowski, deceased, late of Ramat Chen, Israel, by Nicole Horoszowski, legal representative; Daniel Mole, Nancy; Paul Rivat, Saint-Peray, both of France

[73] Assignee: Advanced Technical Fabrication, Marignier, France

[21] Appl. No.: 09/125,244

[22] PCT Filed: Feb. 10, 1997

[86] PCT No.: PCT/FR97/00257

§ 371 Date: Aug. 13, 1998

§ 102(e) Date: Aug. 13, 1998

[87] PCT Pub. No.: WO97/29698

PCT Pub. Date: Aug. 21, 1997

[30] Foreign Application Priority Data

Feb. 13, 1996 [FR] France ................... 96 02002

[51] Int. Cl.[7] .................................................. A61B 17/17
[52] U.S. Cl. ................................................................ 606/80
[58] Field of Search ................................. 606/80, 81, 91, 606/180

[56] References Cited

U.S. PATENT DOCUMENTS

| 4,023,572 | 5/1977 | Weigand et al. ................ 606/81 |
| 4,712,951 | 12/1987 | Brown . |
| 5,100,267 | 3/1992 | Salyer ................................ 606/81 |
| 5,462,548 | 10/1995 | Pappas et al. ..................... 606/81 |
| 5,658,290 | 8/1997 | Lechot .............................. 606/80 |

FOREIGN PATENT DOCUMENTS

| 051359 A1 | 5/1982 | European Pat. Off. . |
| 147339 A2 | 7/1985 | European Pat. Off. . |
| 327509 A1 | 8/1989 | European Pat. Off. . |
| 470912 A2 | 2/1992 | European Pat. Off. . |
| 578322 A2 | 1/1994 | European Pat. Off. . |
| 704191 A1 | 4/1996 | European Pat. Off. . |
| 2281095 | 3/1976 | France . |
| 2500958 | 7/1976 | Germany ......................... 606/81 |
| 3903832 A1 | 8/1990 | Germany . |

OTHER PUBLICATIONS

International Search Report mailed Apr. 22, 1997.

*Primary Examiner*—Jeffrey A. Smith
*Assistant Examiner*—Eduardo C. Robert
*Attorney, Agent, or Firm*—Ratner & Prestia

[57] ABSTRACT

An instrument including a cutter (2) mountable on a cutter spindle (1) and shaped in such a way that it also acts as a test cup 33 engageable by a test head of a femoral prosthesis. The cutter (2) may be attached to the pelvis (34) by means of nails (29), and the cutter position is detected by sighting means (32) on the cutter spindle (1). The sighting means (32) are then used to arrange the final cup in the same position as the cutter (2) so that the position of the final cup may be selected in such a way that the risk of joint dislocation is reduced.

8 Claims, 5 Drawing Sheets

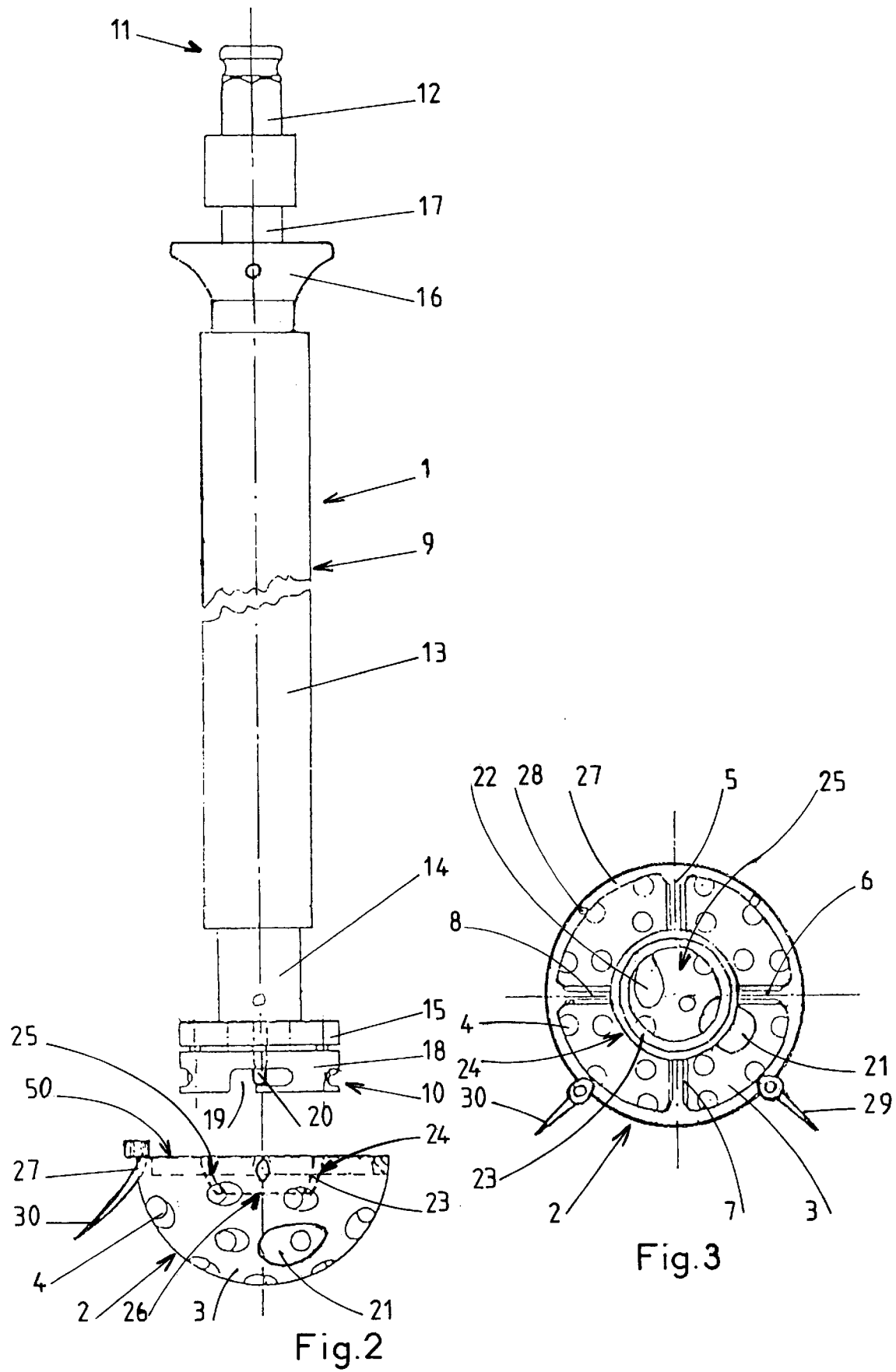

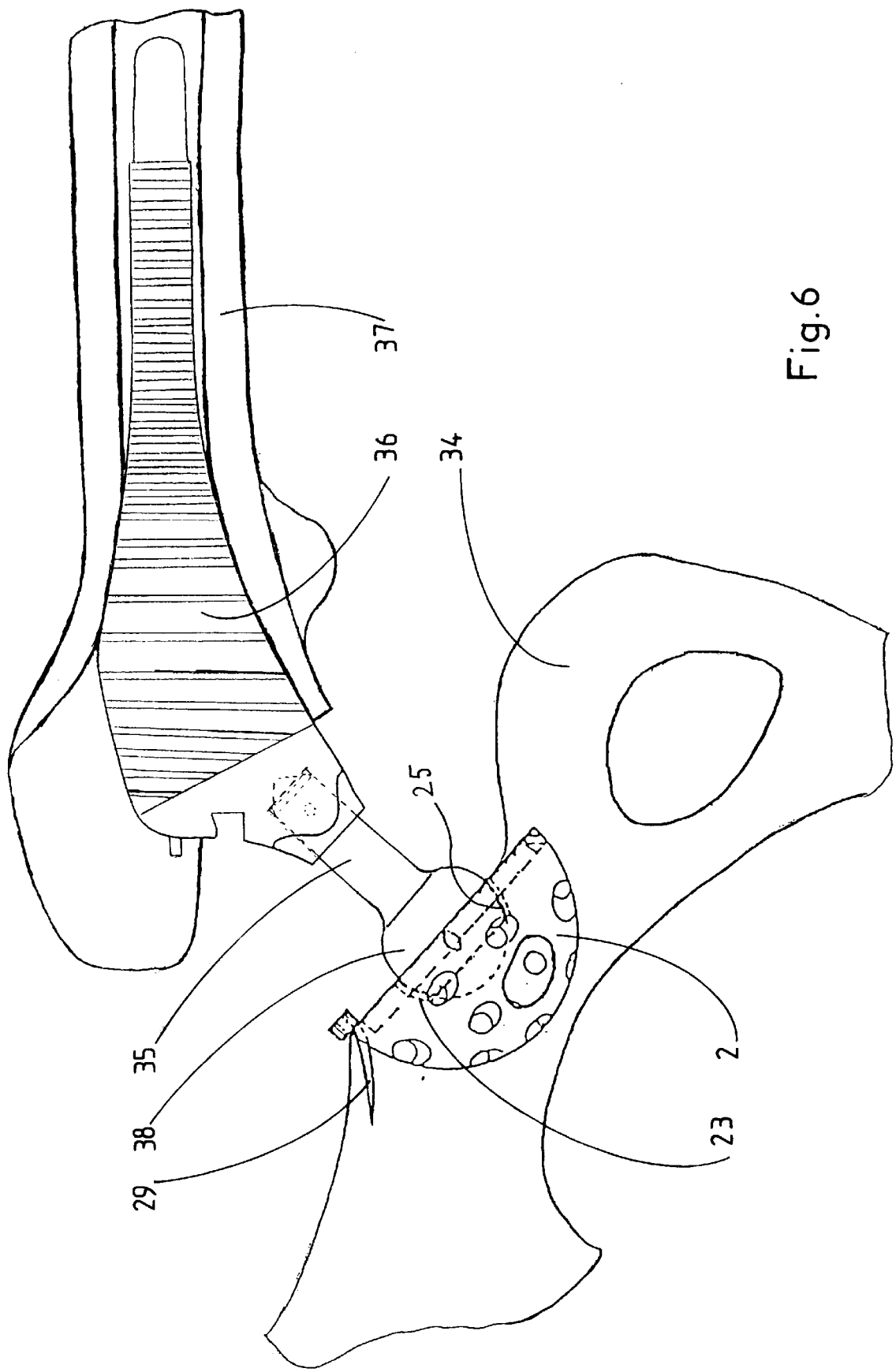

HIP PROSTHESIS POSITIONING INSTRUMENT

This application is the U.S. national phase application of PCT International Application No. PCT/FR97/00257, filed Feb. 10, 1997.

TECHNICAL FIELD OF THE INVENTION

The present invention concerns instruments used to fit hip prostheses, and in particular to fit the cotyloid implants forming the female part of the hip joint.

The first operation of the procedures habitually employed to fit a cotyloid implant is to mill a hemispherical cavity in the acetabulum, using a hemispherical milling tool. A hemispherical milling tool of this kind is described in the document EP-A-0 704 191 published after the priority date, for example, and includes a hollow substantially hemispherical dome with sharp-edged openings and an open base in which are provided radial spacer members to which a milling tool support can be fixed. The milling tool support is a handle with an external handling tube in which is journalled an operating tube in turn mounted to slide longitudinally on a drive shaft. The end of the drive shaft carries a bayonet bush, with L-shape notches at the end arranged around the terminal edge of the bush and shaped to receive and to retain the radial spacer members of the milling tool. The operating tube is attached to a sliding plate carrying locking lugs. A spring presses the operating tube and the sliding plate against the bayonet bush, in which position the locking lugs close the L-shape notches to trap the radial spacer members inserted in the L-shape notches and thereby lock the milling tool. At its other end, the operating tube has an operating ring, that the user can use to unlock the milling tool by causing the operating tube and the sliding plate to slide away from the bayonet bush.

Other milling tools are described in the documents FR-A-2 281 095, EP-A-0 147 339, EP-A-0 327 509, U.S. Pat. No. 4,712,951.

The tools described in all these documents have only a milling use.

The second operation is to fit a test piece into the bone cavity hollowed out by the milling tool, after removing the milling tool. The test piece is the same shape as the final implant to be fitted into the cavity subsequently. The test piece is then removed and the cotyloid implant cemented in place, for example with the help of an impact tool as described in the document EP-A-0 470 912.

In another operation procedure, described for example in the document EP-A-0 051 359, after a first operation identical to the formation of the hemispherical cavity in the bone using a milling tool, a metal cup is forcibly inserted into the cavity. A female test core is introduced into the metal cup, constituting an interface between the metal cup and a femoral prosthesis head. The test core is removed and the final core finally clipped into place.

A first drawback of these techniques is the relative complexity of the instruments, since dedicated test parts are required. Another drawback of these techniques is that the stability of the final joint, conditioned by the orientation of the implant, remains random.

SUMMARY OF THE INVENTION

Accordingly, a first problem to which the invention is addressed is that of simplifying the instruments, enabling test manoeuvring of the joint before final fixing of the prosthesis, without using separate dedicated test parts.

Another problem to which the invention is addressed is that of significantly reducing the residual risks of dislocation of the final joint. The basic idea of the invention is that these residual dislocation risks are the result of the difficulty of checking and fixing the orientation of the final joint relative to the pelvis and the femoral prosthesis of the patient. The invention accordingly provides means for the easy and effective selection, checking and fixing of the orientation of the final implant relative to the pelvis and to the femoral prosthesis of the patient, faithfully reproducing the position assumed by the parts during tests.

To achieve the above and other objects, instruments in accordance with the invention for fitting hip prostheses comprise a milling tool support and at least one milling tool removably attachable to the milling tool support, the milling tool having a hollow substantially hemispherical dome with sharp-edged openings and an open base in which are provided means for removably fixing the milling tool support ;

the substantially hemispherical dome includes additional openings of sufficiently large size to enable checking of contact between the bottom of the cotyloid cavity hollowed out by the milling tool and the hemispherical external surface of the milling tool fitted into said cavity, the milling tool includes a central interior core attached to the substantially hemispherical dome, with an external face separated from the wall of the substantially hemispherical dome to leave a passage for bone fragments cut off by the milling tool, and with an open concentric hemispherical recess at the base of the dome and the inside diameter of which is chosen to correspond to the outside diameter of a femoral prosthesis head to be fitted, the milling tool is associated with means for temporarily fixing the milling tool into the cotyloid cavity formed.

Thus the milling tool itself can constitute a test cotyl, avoiding the need for a dedicated test part.

In an advantageous embodiment, the central interior core is attached to the substantially hemispherical dome by at least two radial spacer members disposed at the base of the dome, said radial spacer members can be used as attachment means of the milling tool on the milling tool support.

In one embodiment, the central interior core is removable, and constituted by an attached part that can be fitted in the dome. Alternatively, the central interior core may be non-removably attached to the dome.

The substantially hemispherical dome preferably includes, at its base, an interior annular peripheral rim with divergent holes in it for temporary fixing spikes.

The milling tool support advantageously comprises a handle a first end of which includes attachment means for removably fastening the milling tool, and the other end of which includes a coupling end-piece enabling selective coupling to the shaft of a drive motor or to a manipulator handle.

The instruments preferably comprise a manipulator handle including sighting means for orienting the milling tool support and the milling tool with a particular anatomical orientation.

The handle with sighting means may advantageously also be adapted to be fitted also to an impaction handle for receiving and implanting the final cotyl, so as to orient the final cotyl with the same orientation as that previously assumed by the milling tool. An arrangement of this kind provides an easy and effective way of choosing, checking and fixing the orientation of the final cotyl relative to the pelvis and to the femoral prosthesis of the patient, to reduce the residual risks of dislocation of the final joint.

BRIEF DESCRIPTION OF THE DRAWINGS

Other objects, features and advantages of the present invention will emerge from the following description of specific embodiments, given with reference to the accompanying figures, in which :

FIG. 2 is a side view of the milling tool-milling tool support assembly from FIG. 1, in the uncoupled position ;

FIG. 3 is a top view of the milling tool from FIGS. 1 and 2 ;

FIG. 6 is a front view of part of the temporary hip joint of the invention during the step of verifying its stability.

DESCRIPTION OF THE PREFERRED EMBODIMENTS

Figure 1:
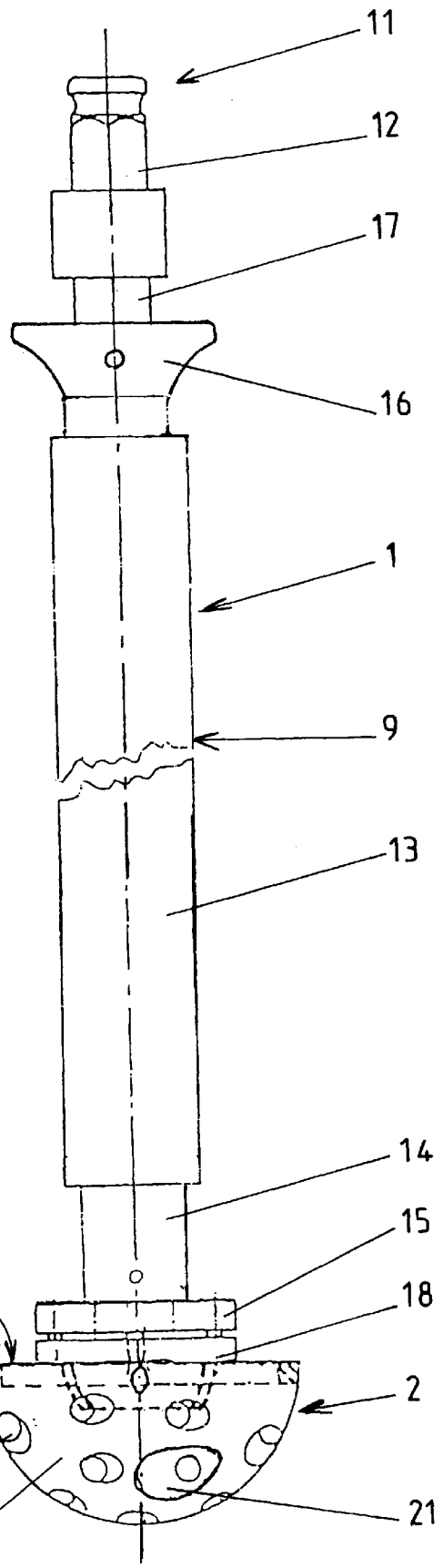
FIG. 1 is a side view of a milling tool and of a milling tool support in accordance with the present invention, in a coupled and locked position.

In the embodiment shown in the figures, instruments in accordance with the invention for fitting hip prostheses comprise a milling tool support 1 and at least one milling tool 2 adapted to be removably fitted to the milling tool support 1.

The milling tool 2 comprises a hollow, substantially hemispherical dome 3, with sharp-edged openings 4 and an open base 50 in which are provided means for removably fixing the milling tool support 1.

In the embodiment shown in the figures, the means for removably fixing the milling tool support 1 comprise radial spacer members 5, 6, 7 and 8 arranged at the base of the dome. There are preferably at least two radial spacer members. There are four of them in the embodiment shown.

The milling tool support 1 includes a handle 9 having at a first end 10 attachment means for removably fastening the milling tool 2, and its other end 11 includes a coupling end-piece 12 for selective coupling to the shaft of a drive motor or a manipulator handle.

The handle 9 of the milling tool support 1 includes an exterior protection tube 13 in which an operating tube 14 is freely journalled. A first end of the operating tube 14 carries a sliding plate 15. The other end of the operating tube 14 carries an operating ring 16, which is accessible to the user for displacing the operating tube 14 in the axial direction.

The handle 9 further comprises a central drive shaft 17 carrying at its first end the coupling end-piece 12, and carrying at its other end a locking bush 18. The locking bush 18 has L-shape slots, in its terminal edge, such as the slot 19, the number of slots being equal to the number of radial spacer members 5–8, and the slots being shaped to constitute a bayonet coupling system for fitting the milling tool 2 to the locking bush 18.

The operating tube 14 slides axially on the drive shaft 17, between a locked position in which the sliding plate 15 is near or bears against the locking bush 18, and an unlocked position in which the sliding plate 15 is away from the locking bush 18.

The sliding plate 15 includes longitudinal lugs, such as the lug 20, closing each of the slots, such as the L-shape slot 19 when the sliding plate 15 is in a locked position. A spring pushes the operating tube 14 towards the locking bush 18. By pulling on the operating ring 16, the user can displace the operating tube 14 against the force exerted by said spring, to disengage the lugs 20 from the L-shape slots 19 to enable the milling tool 2 to be unlocked.

This arrangement is similar to that described in Swiss patent application N° 2933/94-8.

The locking bush 18 has a diameter slightly less than that of the milling tool 2, and so occupies only the peripheral portion of the base 50 of the milling tool, leaving the central part of the base 50 free.

In accordance with the invention, the dome 3 also has additional openings, such as the openings 21 and 22, of sufficiently large size to enable the user to check the contact between the bottom of the cotyloid cavity hollowed out by the milling tool 2 and the hemispherical external surface of the milling tool 2 fitted into the cavity.

The milling tool 2 also includes a central interior core 23, fastened to the substantially hemispherical dome 3, with an external face 24 separated from the wall of the substantially hemispherical dome 3 to provide a passage for bone fragments cut off by the milling tool 2. The central interior core 23 further includes a concentric hemispherical recess 25 open at the base 50 of the dome and the inside diameter of which is chosen to correspond to the outside diameter of a femoral prosthesis head to be fitted. The central interior core 23 is preferably also open at its apex 26 opposite the dome base 50, to expose the central portion of the dome 3 and in particular the openings 21 and 22, and to facilitate the evacuation of bone debris during milling.

The milling tool 2 is associated with means for temporarily fixing the milling tool into the cotyloid cavity formed. As shown in the figures, for example, the substantially hemispherical dome 3 has, at its base 50, an interior annular peripheral rim 27 with divergent holes 28 in it for temporary fixing spikes, for example the spikes 29 and 30.

Figure 4:
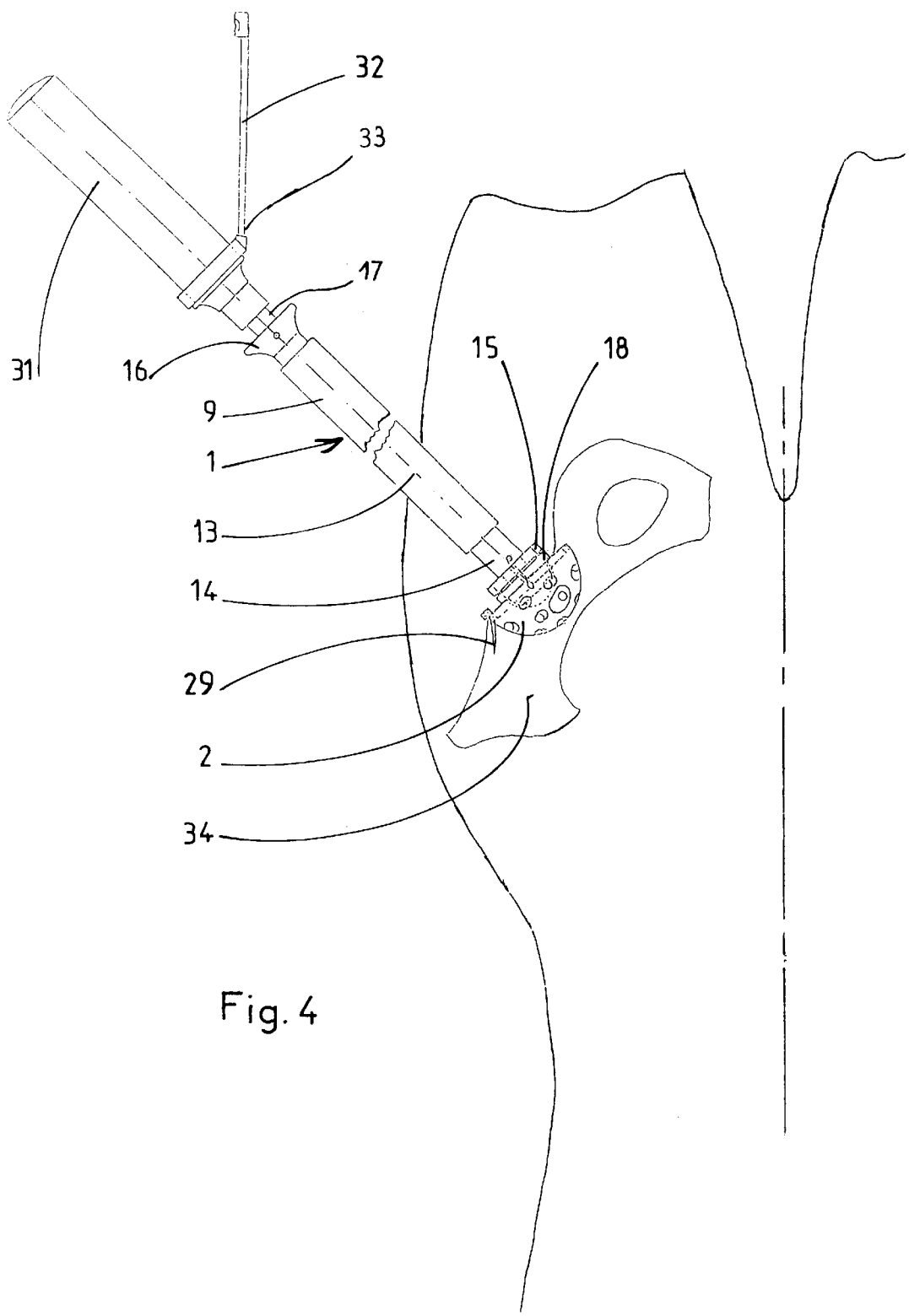
FIG. 4 is a front view of one embodiment of the instruments in accordance with the invention for fitting hip prostheses, used on a patient placed in a lateral decubitus position.
Figure 5:
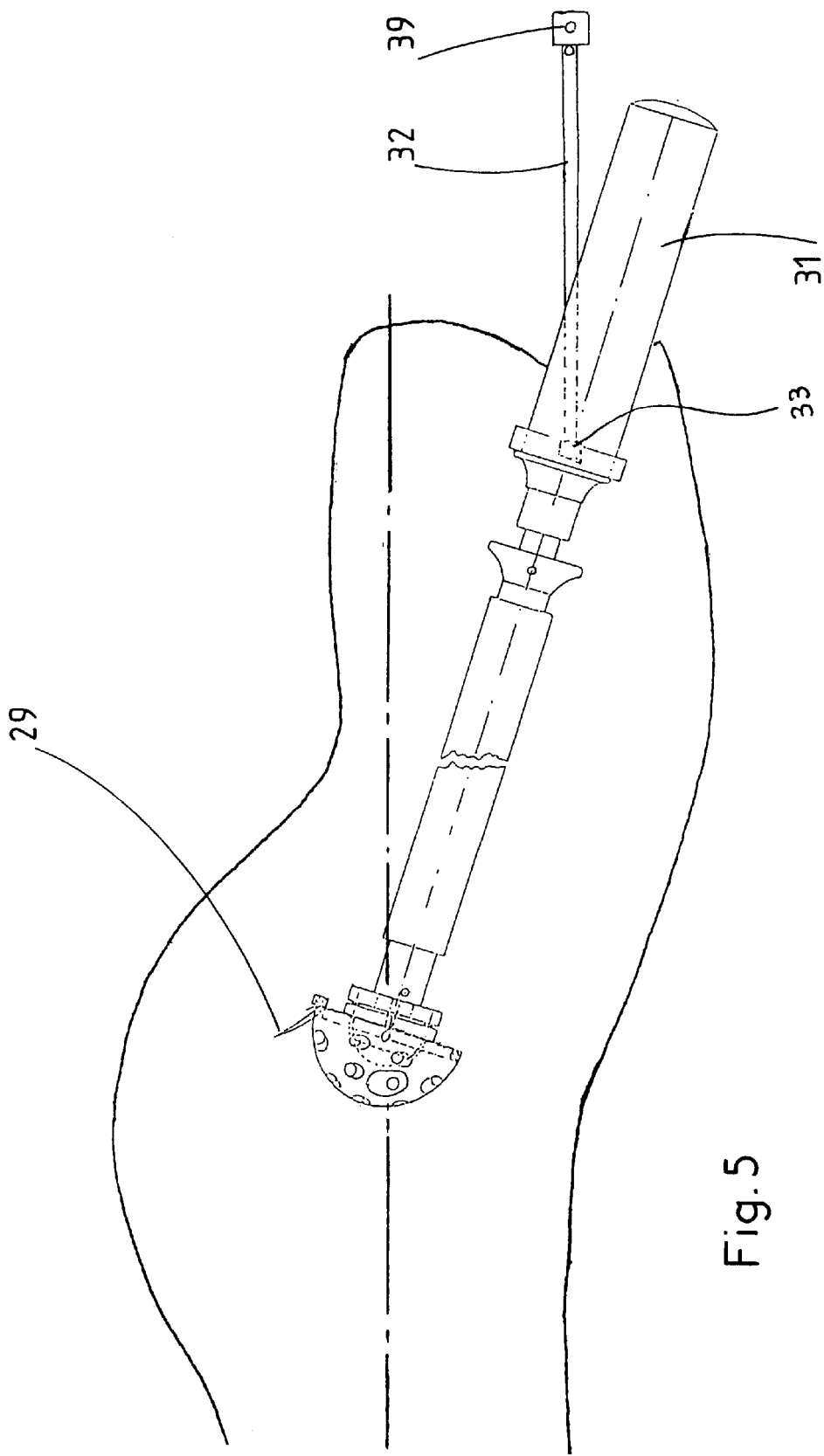
FIG. 5 is a top view of the instruments and of the patient in the FIG. 4 position.

As shown in FIGS. 4 and 5, the instruments of the invention further comprise a manipulator handle 31, adapted to be coupled to the end-piece 12 at the end 11 of the milling tool support 1. The manipulator handle 31 advantageously includes sighting means for orienting the milling tool support 1 and the milling tool 2 in a particular anatomical orientation.

The sighting means comprise a rod 32 articulated at its first end 33 to the manipulator handle 31 and adapted to be locked to the handle 31 in all orientations within an appropriate orientation adjustment range. Alternatively, the rod 32 may be in a fixed orientation relative to the handle 31 at an appropriate angle such that the rod 32 is horizontal when the longitudinal axis of the milling tool support 1 is at an angle of 45° to the horizontal plane and an angle of 15° to the vertical plane containing the rod 32. These angles substantially correspond to the 45° vertical inclination angle of the cotyloid implant, and to the 15° anteversion angle of the cotyloid implant.

The rod 32 preferably incorporates spirit levels 39 showing the orientation of the rod 32 in the horizontal plane.

The instruments further comprise an impaction handle, adapted to receive and to retain the final cotyl at its first end and to receive the manipulator handle 31 at its other end, said handle 31 having sighting means, so that the user can orient the final cotyl with the same orientation as that previously assumed by the milling tool 2.

The instruments previously described can be used in the manner described next with reference to FIGS. 4 through 6.

During a first step, the milling tool 2 is fitted to the milling tool support 1, which is coupled to a motor, not shown, driving axial rotation of the shaft 17 in the operating tube 14 and in the protection tube 13. The motor therefore drives rotation of the milling tool 2 engaged and locked in the locking bush 18 of the milling tool support 1. A hemispherical cavity is made in the bone of the pelvis 34 in this way.

The motor is then uncoupled and the manipulator handle 31 is engaged with the end of the milling tool support 1, with its sighting rod 32. With the patient in a lateral decubitus position, the axis of the milling tool support 1 is oriented so that the rod 32 is horizontal and aligned with the longitudinal axis of the patient, as shown in FIGS. 4 and 5. Accordingly, the axis of the milling tool support 1 is inclined at approximately 45° to the horizontal plane as shown in FIG. 4, and at approximately 15° to the longitudinal axis of the patient as shown from above in FIG. 5. Maintaining this orientation of the milling tool support 1, the milling tool 2 is then fixed into the bone of the pelvis 34 by driving in nails, such as the nail 29.

The milling tool support 1 is then disengaged from the milling tool 2, by manoeuvring the operating ring 16, followed by slight rotation of the milling tool support 1 and movement in translation away from the milling tool 2 to disengage the bayonet coupling.

Then, as shown in FIG. 6, the milling tool 2 may be used as a test cotyl, by placing a test head 35 at the end of a rasp 36 adapted to hollow out in the femur 37 the cavity intended to receive the femoral prosthesis shank. By virtue of the presence of the core 23 with its hemispherical recess 25, the milling tool 2 is itself adapted to receive the spherical end 38 of the test head 35, so constituting a provisional joint enabling the effectiveness of the final joint to be tested, in particular for the absence of any risk of dislocation. In the disposition shown in FIG. 6, the femur 37 of the patient may be moved into all the orientations that are necessary for the habitual movements of the lower limb, and to verify that the test head 35 remains correctly engaged in the milling tool 2. If there is any defect, for example in the event of any risk of dislocation, the test head 35 is removed, the milling tool support 1 and the manipulator handle 31 are fitted to the milling tool 2 again, the nails 29 are removed and the orientation of the milling tool 2 is appropriately modified to reduce the risk of dislocation. The milling tool 2 is fixed again using nails 29. The new orientation of the milling tool 2 is then checked by checking the orientation of the milling tool support 1 relative to the rod 32. The milling tool support 1 is removed and the test head 35 is replaced to check the risk of dislocation again.

When the tests are conclusive, the test head 35 and the milling tool 2 are removed, and replaced by the final cotyl that has the same external shape as the milling tool 2, and an internal cavity with the same shape as the hemispherical recess 25 of the milling tool 2. The final cotyl is fitted using an impaction handle, adapted to be attached to the final cotyl at its first end and to receive the handle 31 with the sighting rod 32 at its other end. At this time it is important to orientate the impaction handle and the final cotyl with the same orientation as that previously assumed by the milling tool support 1 and the milling tool 2, by placing the sighting rod 32 in the same position as that assumed at the time of the last test using the milling tool 2. This ensures that the final cotyl assumes the same orientation as that previously assumed by the milling tool 2 during satisfactory testing of the test head 35. The final implant is then definitively fixed into the acetabulum.

The present invention is not limited to the embodiments that have been explicitly described, but encompasses the various generalisations and variants thereof that fall within the scope of the following claims.

What is claimed is:

1. Instruments for fitting hip prostheses, comprising a milling tool support and at least one milling tool removably attachable to the milling tool support, the milling tool having a hollow substantially hemispherical dome with sharp-edged openings and an open base in which are provided means for removably fixing the milling tool support, wherein:

the substantially hemispherical dome includes additional openings of sufficiently large size to enable checking of contact between the bottom of the cotyloid cavity hollowed out by the milling tool and the hemispherical external surface of the milling tool fitted into said cavity, the milling tool includes a central interior core attached to the substantially hemispherical dome, with an external face separated from the wall of the substantially hemispherical dome to leave a passage for bone fragments cut off by the milling tool, and with an open concentric hemispherical recess at the base of the dome the inside diameter of which is chosen to correspond to the outside diameter of a femoral prosthesis head to be fitted, the milling tool is associated with means for temporarily fixing the milling tool into the cotyloid cavity formed.

2. Instruments according to claim 1, wherein the central interior core is attached to the substantially hemispherical dome by at least two radial spacer members disposed at the base of the dome.

3. Instruments according to claim 1, wherein the central interior core is removable, and constituted by an attached part that can be fitted in the dome.

4. Instruments according to claim 1, wherein the substantially hemispherical dome includes, at its base, an interior annular peripheral rim with divergent holes in it for temporary fixing spikes.

5. Instruments according to claim 1, wherein the milling tool support comprises a handle a first end of which includes attachment means for removably fastening the milling tool, and the other end of which includes a coupling end-piece enabling selective coupling to the shaft of a drive motor or to a manipulator handle.

6. Instruments according to claim 5, wherein they comprise a manipulator handle including sighting means for orienting the milling tool support and the milling tool with a particular anatomical orientation.

7. Instruments according to claim 6, wherein the sighting means comprise a rod articulated at its first end to the manipulator handle and adapted to be locked to the manipulator handle in all orientations within an appropriate orientation adjustment range, and incorporating spirit levels showing the orientation of the rod in the horizontal plane.

8. Instruments according to claim 6, wherein they comprise an impaction handle, adapted to receive and to retain the final cotyl at its first end and to receive at its second end the handle with sighting means, so as to orient the final cotyl with the same orientation as that previously assumed by the milling tool.

* * * * *